(12) United States Patent
Ueda

(10) Patent No.: US 9,669,207 B2
(45) Date of Patent: Jun. 6, 2017

(54) MEDICAL STOPCOCK

(71) Applicant: Terumo Kabushiki Kaisha, Tokyo (JP)

(72) Inventor: Yasuhiro Ueda, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/496,482

(22) Filed: Sep. 25, 2014

(65) Prior Publication Data

US 2015/0013807 A1    Jan. 15, 2015

Related U.S. Application Data

(63) Continuation of application No. PCT/JP2013/058721, filed on Mar. 26, 2013.

(30) Foreign Application Priority Data

Mar. 26, 2012 (JP) .................. 2012-069116

(51) Int. Cl.
  *A61M 39/10* (2006.01)
  *F16K 11/087* (2006.01)
  (Continued)

(52) U.S. Cl.
  CPC ........ *A61M 39/105* (2013.01); *A61M 39/223* (2013.01); *F16K 11/08* (2013.01);
  (Continued)

(58) Field of Classification Search
  CPC .. A61M 39/105; A61M 39/223; A61M 39/22; A61M 2039/224; A61M 2039/229; Y10T 137/86871; F16K 11/08–11/0876
  (Continued)

(56) References Cited

U.S. PATENT DOCUMENTS

| 1,685,236 A | * | 9/1928 | Lawson | ................ F16K 5/0407 |
| | | | | 137/312 |
| 2007/0232989 A1 | * | 10/2007 | Kitani | ................... A61M 39/02 |
| | | | | 604/28 |

(Continued)

FOREIGN PATENT DOCUMENTS

| JP | 2003-159336 A | 6/2003 |
| JP | 2008-511371 A | 4/2008 |

(Continued)

OTHER PUBLICATIONS

International Search Report dated Jun. 18, 2013 issued in Application No. PCT/JP2013/058721.

*Primary Examiner* — Laura Bouchelle
*Assistant Examiner* — Anh Bui
(74) *Attorney, Agent, or Firm* — Foley & Lardner LLP

(57) ABSTRACT

A medical stopcock device comprises a housing configured to allow a flow of liquid therethrough, and a cock configured to fit in the housing and switch flow paths of the liquid flowing through the housing. The housing comprises a cylindrical body section formed with a through-hole, an upstream port section provided on an outer periphery of the body section, a downstream port section provided on the outer periphery of the body section and disposed on a side of the body section that is opposite to the upstream port section, and a side tube port section provided between the upstream port section and the downstream port section on the outer periphery of the body section and including a first communication hole, and a second communication hole having an opening area smaller than an opening area of the first communication hole. The cock comprises a cylindrical section configured to be inserted in the through-hole of the body section in a slidable manner, and including a first flow path groove and a second flow path groove, and a handle section configured to rotate the cylindrical section. When the (Continued)

cock is at a reference position, the upstream port section, the side tube port section, and the downstream port section communicate with each other in a manner such that the first flow path groove communicates with the upstream port section and the first communication hole in the side tube port section, and the second flow path groove communicates with the second communication hole in the side tube port section and the downstream port section.

13 Claims, 10 Drawing Sheets

(51) Int. Cl.
    *F16K 11/085*     (2006.01)
    *F16K 11/083*     (2006.01)
    *F16K 11/08*     (2006.01)
    *F16K 31/60*     (2006.01)
    *A61M 39/22*     (2006.01)
    *A61M 39/24*     (2006.01)

(52) U.S. Cl.
    CPC .......... *F16K 11/083* (2013.01); *F16K 11/085* (2013.01); *F16K 11/087* (2013.01); *F16K 11/0836* (2013.01); *F16K 11/0853* (2013.01); *F16K 11/0856* (2013.01); *F16K 11/0873* (2013.01); *F16K 11/0876* (2013.01); *F16K 31/60* (2013.01); *A61M 2039/224* (2013.01); *A61M 2039/229* (2013.01); *A61M 2039/2426* (2013.01); *Y10T 137/86871* (2015.04)

(58) Field of Classification Search
    USPC ................. 251/209; 137/602, 625.32, 625.4, 137/625.41, 625.46, 861, 862; 604/32, 604/99.04, 167.05, 236, 246, 247, 248, 604/249, 250, 256
    See application file for complete search history.

(56) References Cited

U.S. PATENT DOCUMENTS

| | | | |
|---|---|---|---|
| 2007/0287953 A1* | 12/2007 | Ziv | ..................... A61M 39/223 604/31 |
| 2010/0191106 A1 | 7/2010 | Koyama | |
| 2014/0018746 A1 | 1/2014 | Ueda et al. | |

FOREIGN PATENT DOCUMENTS

| | | |
|---|---|---|
| WO | WO-2006/025054 A2 | 3/2006 |
| WO | WO-2008/155938 A1 | 12/2008 |
| WO | WO-2012/133100 A1 | 10/2012 |

* cited by examiner

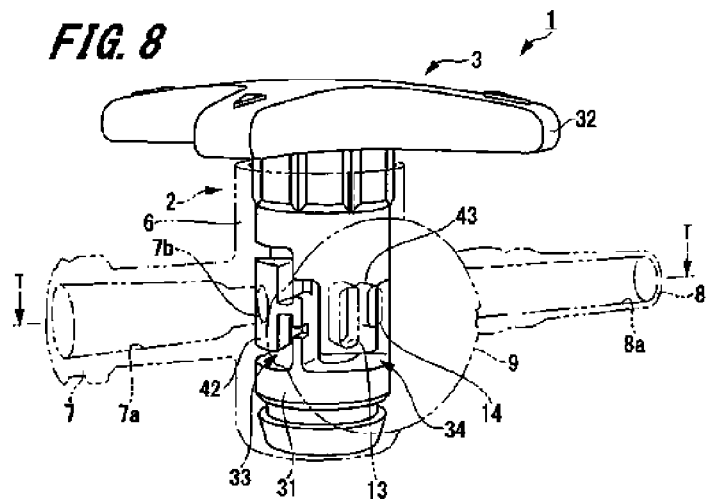
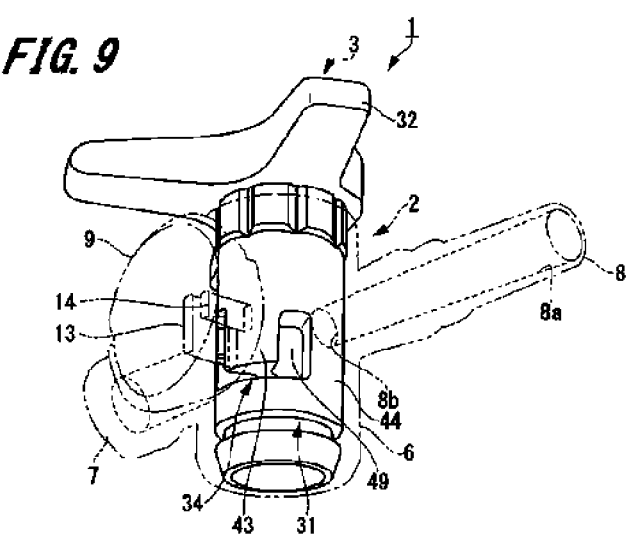

MEDICAL STOPCOCK

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/058721 filed on Mar. 26, 2013, which is based upon and claims the benefit of priority of Japanese Application No. 2012-069116 filed on Mar. 26, 2012, the entire contents of which are hereby incorporated by reference in their entireties.

BACKGROUND

Technical Field

The present disclosure relates to a medical stopcock, which is connected to various medical instruments, infusion containers or the like, and which is capable of switching flow paths arbitrarily.

Background Art

Conventionally, upon performing fluid infusion, blood transfusion, hemodialysis or the like, a liquid is infused into the body by using a medical tube. In order to change flow paths for injecting a medical solution or to mix a plurality of medical solutions and inject the mixed medical solution, a medical stopcock is used.

Conventional medical stopcocks of this type include a medical stopcock described in Japanese Patent Application Publication 2003-159336, for example. The medical stopcock disclosed in Japanese Patent Application Publication 2003-159336 includes a cylindrical body and a stopper. The cylindrical body has a plurality of branches, which are an upstream port section, a downstream port section, and a port section for a side tube. The stopper has a columnar-shaped cock rotatably fitted in the cylindrical body. The stopper is formed with a flow path switching groove including a plurality of longitudinal grooves and is an arc-shaped groove. The stopper having a cock is rotated so as to switch flow paths of liquid passing through the cylindrical body.

A connector is generally attached to the opening of a port section for a side tube to liquid-tightly connect a male connector of a syringe, a lure taper member or the like. The connector includes a valve formed with a slit and a holding member for holding the valve. Through the connector, a medical solution for mixture is injected to the port section for a side tube. In a state where a male connector of a syringe, a lure taper member or the like is not connected to the connector, the port section for a side tube is closed by the valve.

However, in the technique disclosed in Japanese Patent Application Publication 2003-159336, the arc-shaped groove is formed continuously from the upstream port section to the downstream port section. Thus, when all of the ports communicate with each other, a medical solution flowing in from the upstream port section does not flow to the port section for a side tube but flows to the downstream port section. Therefore, when the valve attached to the port section for a side tube is closed, a flow of a medical solution is hardly generated in the port section for a side tube.

As a result, according to the technique described in Japanese Patent Application Publication 2003-159336, a medical solution injected from the port section for a side tube disadvantageously stays in the internal space of the port section for a side tube or in a space formed between the connector and the port section for a side tube when the valve is closed.

In addition, from the port section for a side tube, vasopressor solution and depressor solution, which vary blood pressure, may be injected as medical solutions. When depressor solution is injected from the port section for a side tube in a state where vasopressor solution stays in the port section for a side tube, the staying vasopressor solution may be pushed by depressor solution, causing an inconvenience.

SUMMARY OF INVENTION

In light of the foregoing, one objective of certain embodiments of the present invention is to provide a medical stopcock capable of preventing a medical solution that has been injected from the port section for a side tube from staying in the internal space of the port section for a side tube even when the connector attached to the port section for a side tube is closed.

According to one embodiment of the present invention, a medical stopcock includes: a housing, which liquid flows through, and a cock, which is fitted in the housing and switches flow paths of the liquid flowing through the housing.

The housing includes: a cylindrical body section formed with a through-hole; an upstream port section; a downstream port section; and a port section for a side tube. The upstream port section is provided on an outer peripheral of the body section. The downstream port section is provided on the outer peripheral of the body section and arranged on a side opposite to the upstream port section across the body section. The port section for a side tube is provided between the upstream port section and the downstream port section on the outer peripheral of the body section and formed with a first communication hole and a second communication hole having an opening area smaller than that of the first communication hole.

The cock includes: a cylindrical section which is inserted in the through-hole of the body section in a slidable manner; and a handle section for rotating the cylindrical section. The cylindrical section is formed with a first flow path groove and a second flow path groove through which the liquid passes.

In a state where the cock is at a reference position making the upstream port section, the port section for a side tube, and the downstream port section communicate with each other, the first flow path groove communicates with the upstream port section and the first communication hole in the port section for a side tube. In addition, the second flow path groove communicates with the second communication hole in the port section for a side tube and the downstream port section.

Since the port section for a side tube communicates with the upstream port section through the first communication hole and the first flow path groove, and communicates with the downstream port section through the second communication hole and the second flow path groove, a medical solution flowing in from the upstream port section can be made to flow in the port section for a side tube. In addition, since the second communication hole has an opening area smaller than that of the first communication hole, the medical solution flowing in the port section for a side tube can be prevented from being discharged to the downstream port section directly through the second communication hole and the second flow path groove.

As a result, a flow path passing through the port section for a side tube is formed, whereby a medical solution staying in the port section for a side tube can be pushed by a medical solution flowing from the upstream port section.

According to embodiments of the medical stopcock of the present invention, a medical solution injected from the port section for a side tube can be prevented from staying in the port section for a side tube even when the valve of the connector attached to the port section for a side tube is closed.

BRIEF DESCRIPTION OF DRAWINGS

FIG. 8 is a perspective view illustrating the medical stopcock according to an embodiment of the present invention in a state where a flow of liquid is stopped.

FIG. 9 is a perspective view of the medical stopcock illustrated in FIG. 8 viewed from the downstream port side.

DETAILED DESCRIPTION

Figure 1:
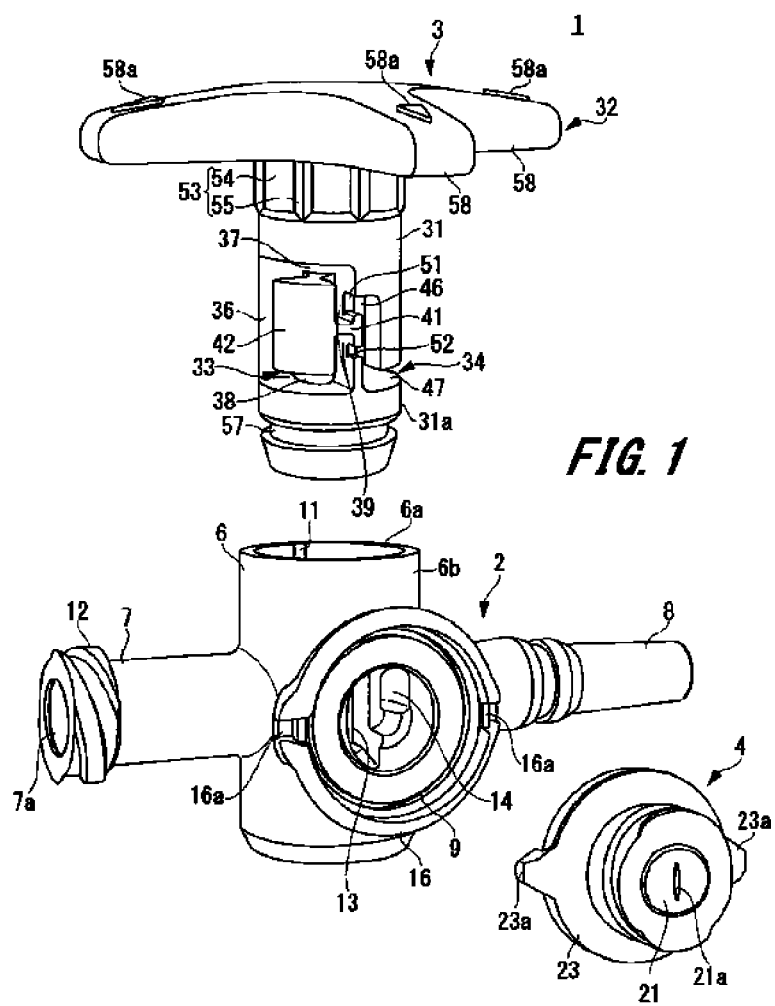
FIG. 1 is an exploded perspective view illustrating a medical stopcock according an embodiment of the present invention.

Hereinafter, embodiments of a medical stopcock according to the present invention will be described with reference to FIGS. 1 to 12. Note that, in the drawings, the same components are denoted by the same reference numerals. The present invention is not limited to the embodiments described below.
Embodiment of Medical Stopcock
Configuration Example of Medical Stopcock First, a Configuration Example of an embodiment (hereinafter, referred to as the "Embodiment") of a medical stopcock according to the present invention will be described with reference to FIGS. 1 to 4.

Figure 2:
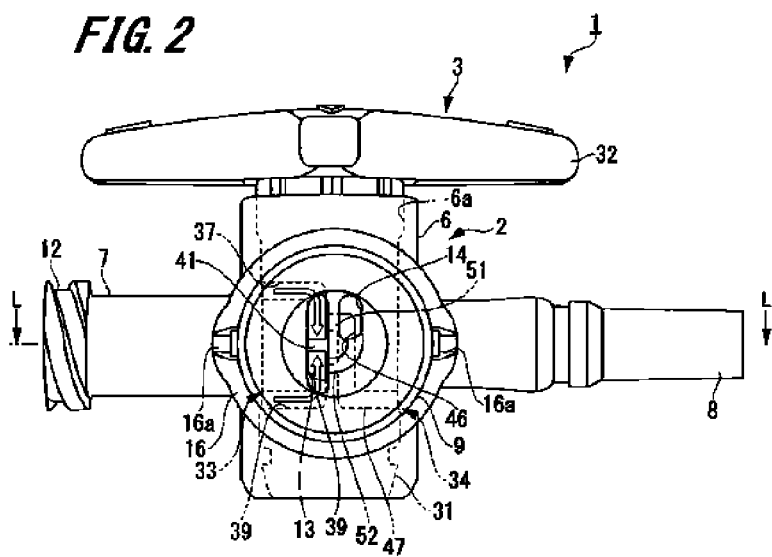
FIG. 2 is a front view illustrating the medical stopcock according to an embodiment of the present invention.
Figure 3:
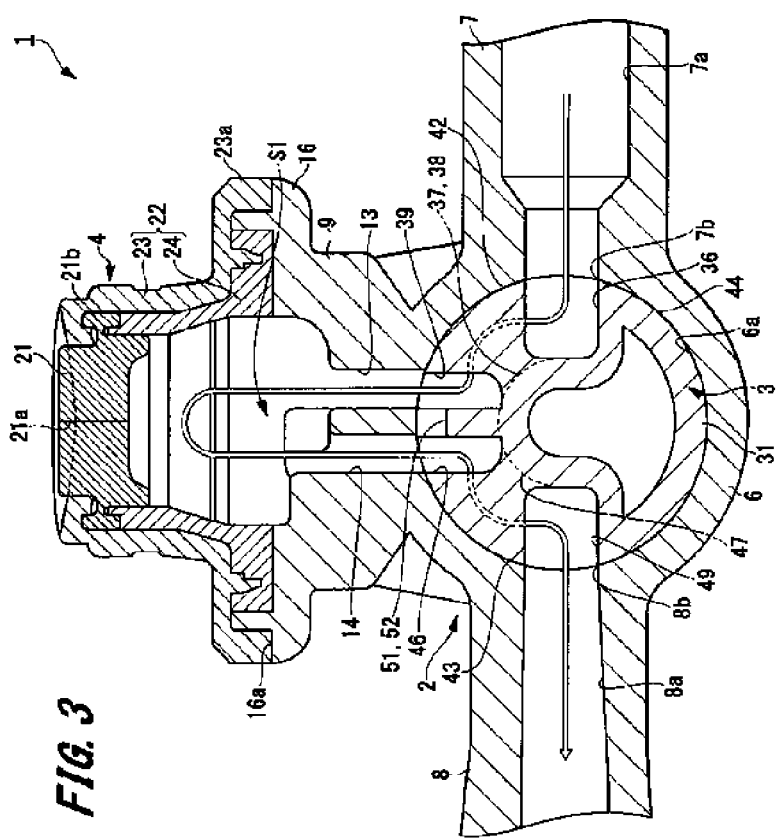
FIG. 3 is a cross-sectional view taken along line L-L of FIG. 2.

FIG. 1 is an exploded perspective view illustrating a medical stopcock of the Embodiment, FIG. 2 is a front view illustrating the medical stopcock of the Embodiment, and FIG. 3 is a cross-sectional view taken along line L-L of FIG. 2.

A medical stopcock 1 illustrated in FIG. 1 is used for changing flow paths of a medical solution or for mixing a plurality of medical solutions and injecting the medical solution or mixed medical solutions. The medical stopcock 1 includes a housing 2 through which liquid (medical solution) flows, and a cock 3 fitted in the housing 2. To the housing 2 of the medical stopcock 1, a connector 4 for liquid-tightly connecting a male connector of a syringe, a lure taper member, or the like is attached.

A medical solution flowing through the housing 2 may be liquid including solids such as colloidal particles as well as perfect liquid.

Examples of the material of the housing 2 and the cock 3 include polyolefins such as polyethylene, polypropylene, ethylene-propylene copolymers, and ethylene-vinyl acetate copolymers (EVA) and the like, polyvinyl chloride, polyvinylidene chloride, polystyrene, polyamide, polyimide, polyamide-imide, polycarbonate, poly(4-methylpentene-1), ionomers, acrylic resins, polymethyl methacrylate, acrylonitrile-butadienestyrene copolymer (ABS resin), acrylic-styrene copolymers (AS resins), butadiene styrene copolymers, polyesters such as polyethylene terephthalate (PET), polybutylene terephthalate (PBT), polycyclohexane terephthalate (PCT), polyether, polyether ketone (PEK), polyether ether ketone (PEEK), polyether imide, polyacetal (POM), polyphenylene oxide, denatured polyphenylene oxide, polysulfone, polyether sulfone, polyphenylene sulfide, polyarylate, aromatic polyester (liquid crystal polymers), polytetrafluoroethylene, polyvinylidene fluoride, and other fluororesins, a blended material or a polymer alloy each having at least one of the aforesaid materials as a component thereof. Examples of the material of the housing 2 also include various kinds of glass materials, ceramic materials, and metallic materials.
Housing The housing 2 illustrated in FIGS. 1 and 2 includes a cylindrical body section 6, an upstream port section 7 into which a medical solution flows, a downstream port section 8 from which the medical solution flows, and a port section 9 for a side tube into which a medical solution different from the medical solution flowing through the upstream port section 7 and the downstream port section 8 is injected.

The body section 6 is formed in a substantially cylindrical shape having both ends open and is formed with a through-hole 6a penetrating through the body section 6 in the axial direction thereof. On the inner wall of the through-hole 6a, an engagement projection 11 is provided. The engagement projection 11 is formed at one end of the body section 6 in the axial direction. On an outer peripheral surface 6b of the body section 6, the upstream port section 7, the downstream port section 8, and the port section 9 for a side tube are formed.

The upstream port section 7 projects substantially perpendicularly from the outer peripheral surface 6b of the body section 6. The upstream port section 7 is formed in a substantially cylindrical shape. As illustrated in FIG. 3, a tube hole 7a of the upstream port section 7 communicates with the through-hole 6a of the body section 6. Therefore, in the inner peripheral surface of the through-hole 6a, an upstream opening 7b, which is a flow path end of the upstream port section 7, is formed.

The tube hole 7a functions as a flow path through which a medical solution flows through the housing. In addition, as illustrated in FIG. 1, on the end of the upstream port section 7 opposite to the body section 6, a screw portion 12 for connecting with a tube, a connector, or another medical stopcock is formed.

As illustrated in FIG. 2, on the side opposite to the upstream port section 7 across the body section 6, the downstream port section 8 is arranged. The downstream port section 8 is formed in a substantially cylindrical shape and projects substantially perpendicularly from the outer peripheral surface 6b of the body section 6. As illustrated in FIG. 3, a tube hole 8a of the downstream port section 8 communicates with the through-hole 6a of the body section 6 similarly to the upstream port section 7. Therefore, in the inner peripheral surface of the through-hole 6a, a downstream opening 8b, which is a flow path end of the downstream port section 8, is formed. The tube hole 8a is a flow path through which a medical solution flows through the housing 2.

As illustrated in FIG. 2, the port section 9 for a side tube is arranged between the upstream port section 7 and the downstream port section 8. More specifically, the upstream port section 7, the port section 9 for a side tube, and the downstream port section 8 are arranged on the outer peripheral surface 6b of the body section 6 along the circumferential direction of the body section 6 at substantially 90° intervals. The port section 9 for a side tube is formed in a substantially columnar shape.

In the port section 9 for a side tube, a first communication hole 13 and a second communication hole 14 penetrating through the port section 9 for a side tube along the axial direction is formed. Through the first communication hole 13 and the second communication hole 14, a medical solution flowing from the upstream port section 7 and the downstream port section 8 and a medical solution injected from a male connector of a syringe, a lure taper member, or the like attached to the connector 4 to be described later (refer to FIG. 3) pass.

The first communication hole 13 is formed on the upstream port section 7 side and the second communication hole 14 is formed on the downstream port section 8 side. The total length of the first communication hole 13 and the second communication hole 14 in the circumferential direction of the body section 6 is set substantially identical to the diameter of the upstream opening 7b and the downstream opening 8b. An opening area of the second communication hole 14 is set smaller than an opening area of the first communication hole 13. These first communication hole 13 and second communication hole 14 communicate with the through-hole 6a of the body section 6.

At the end of the port section 9 for a side tube opposite to the body section 6, a ring-like fitting recess 16 is formed. The fitting recess 16 is provided at the outer edge of the end of the port section 9 for a side tube. In the fitting recess 16, lock receiving parts 16a are provided. The lock receiving parts 16a are formed by cutting off parts of the fitting recess 16, for example.

As illustrated in FIG. 3, in the fitting recess 16, the connector 4 is fitted to cover the openings of the first communication hole 13 and the second communication hole 14. By fitting the connector 4 in the fitting recess 16, the openings of the first communication hole 13 and the second communication hole 14 on the fitting recess 16 side are closed by the connector 4 when not in use.

Connector

The connector 4 includes a valve 21 and a holding part 22 for holding the valve 21. The valve 21 is formed to be elastically deformable. Examples of the material of the valve 21 include various kinds of rubber such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluorocarbon rubber, various kinds of thermoplastic elastomers such as a styrene-based elastomer, a polyolefine-based elastomer, a polyvinyl chloride-based elastomer, a polyurethane-based elastomer, a polyester-based elastomer, a polyamide-based elastomer, a polybutadine-based elastomer, and a fluorocarbon rubber-based elastomer. Examples of the material of the valve 21 also include a blended material having one, two or more of the aforementioned materials as the components thereof.

The valve 21 is formed in a substantially columnar shape. The valve 21 is formed with a slit 21a in which the tip end of the male connector is inserted. In addition, as illustrated in FIG. 3, on the side surface portion of the valve 21, a fixing portion 21b for fixing to the holding part 22 is provided.

The holding part 22 includes a first member 23 and a second member 24 joined to the first member 23. The valve 21 is fixed by sandwiching the fixing portion 21b of the valve 21 between the first member 23 and the second member 24. The first member 23 and the second member 24 are fixed by a fixing method such as adhesive, fusion, a fixing screw, and the like.

The first member 23 is formed with a locking claw 23a for locking in the lock receiving part 16a of the fitting recess 16. The holding part 22 is then fitted in the fitting recess 16 so as to be joined to the port section 9 for a side tube. Note that, the holding part 22 may be fixed to the port section 9 for a side tube by a fixing method such as adhesive, fusion, a fixing screw, and the like.

Cock

Figure 4:
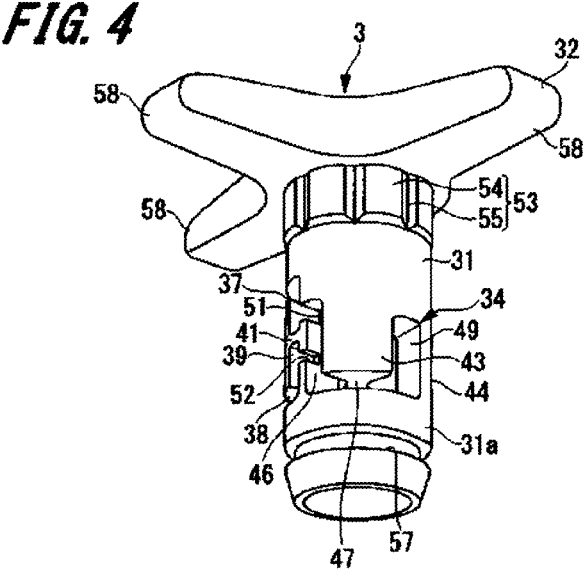
FIG. 4 is a perspective view illustrating a cock of the medical stopcock according to an embodiment of the present invention.
Figure 5:
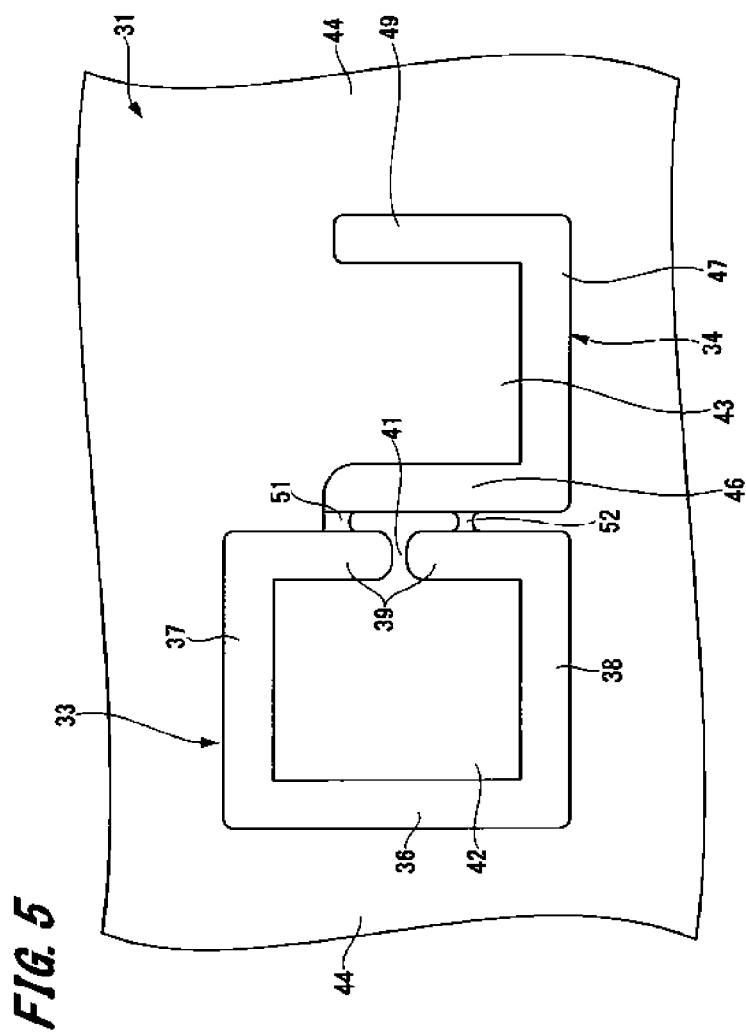
FIG. 5 is a development view illustrating a flow path groove formed in the cock of the medical stopcock according to an embodiment of the present invention.

Next, the cock 3 is described with reference to FIGS. 1 to 5. FIG. 4 is a perspective view illustrating the cock 3, and FIG. 5 is a development view illustrating the side surface of the cock 3.

The cock 3 is fitted in the body section 6 of the housing 2 and switches flow paths of flow in the housing 2. As illustrated in FIGS. 1 and 4, the cock 3 includes a cylindrical section 31 and a handle section 32 for rotating the cylindrical section 31.

The cylindrical section 31 is formed in a substantially columnar shape. The outer diameter of the cylindrical section 31 is set substantially identical to the inner diameter of the through-hole 6a of the body section 6. The cylindrical section 31 is inserted in the through-hole 6a of the body section 6, and a side wall 31a of the cylindrical section 31 is in close contact with the inner peripheral surface of the through-hole 6a in a slidable manner. The cylindrical section 31 is supported by the body section 6 in a rotatable manner along the circumferential direction of the body section 6.

In the side wall 31a of the cylindrical section 31, a first flow path groove 33 and a second flow path groove 34 are formed. The first flow path groove 33 and the second flow path groove 34 are formed to be recessed in the radially inward direction from the side wall 31a of the cylindrical section 31 respectively.

As illustrated in FIG. 5, the first flow path groove 33 includes a first liquid introduction section 36, two communication sections 37 and 38, and a first liquid discharge section 39. The first liquid introduction section 36 is a longitudinal groove section formed along the axial direction of the cylindrical section 31. The length of the first liquid introduction section 36 in the axial direction of the cylindrical section 31 is set longer than the diameter of the upstream opening 7b and the downstream opening 8b, and the lengths of the first communication hole 13 and the second communication hole 14 in the axial direction of the body section 6 (refer to FIG. 6).

From one end of the first liquid introduction section 36 in the axial direction of the cylindrical section 31, a first communication section 37 is formed continuously, and from the other end thereof in the axial direction of the cylindrical section 31, a second communication section 38 is formed continuously.

The first communication section 37 is formed on one side in the axial direction of the cylindrical section 31 along the circumferential direction of the cylindrical section 31 to have a predetermined length. The second communication section 38 is formed on the other side in the axial direction of the cylindrical section 31 along the circumferential direction of the cylindrical section 31 to have a length substantially identical to that of the first communication section 37. Note that, the length of the first communication section 37 and the second communication section 38 in the circumferential direction of the cylindrical section 31 is set longer than the diameter of the upstream opening 7b and the downstream opening 8b, and the length of the first communication hole 13 and the second communication hole 14 in the circumferential direction of the body section 6.

On the end of the first communication section 37 and the second communication section 38 opposite to the first liquid introduction section 36 in the circumferential direction of the cylindrical section 31, the first liquid discharge section 39 is formed.

At the first liquid discharge section 39, the first communication section 37 and the second communication section 38 are merged. Meanwhile, at a part where the first communication section 37 and the second communication section 38 are merged at the first liquid discharge section 39, a projection 41 is formed. The projection 41 projects from the wall surface, which is radially inward, of the first flow path groove 33 to the height of substantially identical level to the side wall 31a of the cylindrical section 31.

Note that, the object of embodiments of the present invention can be achieved without providing the projection 41 at a part where the first communication section 37 and the second communication section 38 are merged at the first liquid discharge section 39.

By providing the first communication section 37 and the second communication section 38 in the first flow path groove 33, turbulent flow easily occurs upon merging of a medical solution flowing from the first communication section 37 into the first liquid discharge section 39 and a medical solution flowing from the second communication section 38 into the first liquid discharge section 39, whereby medical solutions can be prevented from staying.

A part of the side wall 31a of the cylindrical section 31 surrounded by the first liquid introduction section 36, the first communication section 37, the second communication section 38, and the first liquid discharge section 39 included in the first flow path groove 33 is a first closing surface 42. More specifically, the first flow path groove 33 is formed avoiding the first closing surface 42. The size and position of the first closing surface 42 are set such that the first closing surface 42 can close the upstream opening 7b, the downstream opening 8b, the first communication hole 13, and the second communication hole 14 (refer to FIG. 8).

Near the first flow path groove 33, the second flow path groove 34 is arranged. The second flow path groove 34 includes a second liquid introduction section 46, a third communication section 47, and a second liquid discharge section 49.

As illustrated in FIG. 4, the second liquid introduction section 46 is arranged near the first liquid discharge section 39.

As illustrated in FIG. 2, the positional relationship between the first liquid discharge section 39 and the second liquid introduction section 46 corresponds to the positional relationship between the first communication hole 13 and the second communication hole 14 formed in the port section 9 for a side tube. The length of the cylindrical section 31 in the circumferential direction from the first liquid discharge section 39 to the second liquid introduction section 46 is set substantially identical to the diameter of the upstream opening 7b and the downstream opening 8b (refer to FIG. 11).

As illustrated in FIG. 5, the second liquid introduction section 46 is a longitudinal groove section formed substantially parallel to the first liquid discharge section 39 and along the axial direction of the cylindrical section 31. The length of the second liquid introduction section 46 in the axial direction of the cylindrical section 31 is set longer than the diameter of the upstream opening 7b and the downstream opening 8b, and the length of the first communication hole 13 and the second communication hole 14 in the axial direction of the body section 6.

The second liquid introduction section 46 and the first liquid discharge section 39 communicate with each other through two connection grooves 51 and 52. The first connection groove 51 is formed on the first communication section 37 side of the first liquid discharge section 39, and the second connection groove 52 is formed on the second communication section 38 side of the first liquid discharge section 39.

The two connection grooves 51 and 52 are formed by cutting off the side wall 31a of the cylindrical section 31 between the second liquid introduction section 46 and the first liquid discharge section 39, for example. The opening area of each of the two connection grooves 51 and 52 in the radial direction of the cylindrical section 31 is set smaller than the opening area of the first communication hole 13 and the opening area of the second communication hole 14.

In addition, from the other end of the second liquid introduction section 46 in the axial direction of the cylindrical section 31, the third communication section 47 is formed continuously. The third communication section 47 is formed in the direction opposite to the first flow path groove 33 in the circumferential direction of the cylindrical section 31. The length of the third communication section 47 in the circumferential direction of the cylindrical section 31 is set longer than the diameter of the upstream opening 7b and the downstream opening 8b and the length of the first communication hole 13 and the second communication hole 14 in the circumferential direction of the body section 6.

At the end of the third communication section 47 opposite to the second liquid introduction section 46 in the circumferential direction of the cylindrical section 31, the second liquid discharge section 49 is formed continuously.

The second liquid discharge section 49 is a longitudinal groove section extending along the axial direction of the cylindrical section 31. The length of the second liquid discharge section 49 in the axial direction of the cylindrical section 31 is set longer than the diameter of the upstream opening 7b and the downstream opening 8b, and the length of the first communication hole 13 and the second communication hole 14 in the axial direction of the body section 6. The second liquid discharge section 49 is formed at a position substantially 180° away from the first liquid introduction section 36 along the circumferential direction of the cylindrical section 31.

A part of the side wall 31a of the cylindrical section 31 surrounded by the second liquid introduction section 46, the third communication section 47, and the second liquid discharge section 49 included in the second flow path groove 34 is a second closing surface 43. More specifically, the second flow path groove 34 is formed avoiding the second closing surface 43. The size and position of the second closing surface 43 are set such that the second closing surface 43 can close the upstream opening 7b, the downstream opening 8b, and the first and second communication holes 13 and 14 formed in the port section 9 for a side tube (refer to FIG. 9).

The first liquid introduction section 36, the first liquid discharge section 39 and the second liquid introduction section 46, and the second liquid discharge section 49 are arranged at substantially 90° interval along the circumferential direction of the cylindrical section 31. More specifically, the positional relationship between the first liquid introduction section 36, the first liquid discharge section 39 and the second liquid introduction section 46, and the second liquid discharge section 49 corresponds to the positional relationship of the upstream port section 7, the downstream port section 8, and the port section 9 for a side tube formed in the housing 2.

A part of a surface of the side wall 31a of the cylindrical section 31 that is between the first liquid introduction section 36 and the second liquid discharge section 49 and that is opposite to the first liquid discharge section 39 and the second liquid introduction section 46 is a third closing surface 44. The first closing surface 42, the second closing surface 43, and the third closing surface 44 close not only the upstream opening 7b and the downstream opening 8b but also openings of the first communication hole 13 and the second communication hole 14 formed in the port section 9 for a side tube when the cylindrical section 31 is rotated by a predetermined amount with respect to the body section 6 (refer to FIG. 9).

Note that, for the second flow path groove 34, a plurality of communication sections may be formed similarly to the first flow path groove 33.

As illustrated in FIGS. 1 and 4, at one end of the cylindrical section 31 in the axial direction, an engagement receiving part 53 is provided. The engagement receiving part 53 includes a plurality of (eight in the Embodiment) swelling parts 54 each formed in substantially trapezoidal shape and engagement recesses 55. The plurality of swelling parts 54 are formed along the circumferential direction of the cylindrical section 31. Therefore, between each adjacent two of the plurality of swelling parts 54, each of the engagement recesses 55 is formed. To the engagement recesses 55, the engagement projection 11 provided on the body section 6 engages.

On the other side of the cylindrical section 31 in the axial direction, that is, on the opposite side of the engagement receiving part 53, a lock groove 57 is formed. The lock groove 57 is formed continuously along the circumferential direction of the cylindrical section 31. The lock groove 57 is locked with a lock flange, which is not illustrated, provided on the inner peripheral surface of the through-hole 6a when, the cylindrical section 31 is inserted in the through-hole 6a of the body section 6. The cylindrical section 31 thereby can be prevented from slipping out from the through-hole 6a of the body section 6.

On one end of the cylindrical section 31 in the axial direction, a T-shaped handle section 32 for rotary operation of the cylindrical section 31 is formed. The handle section 32 includes three levers 58. The three levers 58 are formed at positions respectively corresponding to the first liquid introduction section 36, the first liquid discharge section 39 and the second liquid introduction section 46, and the second liquid discharge section 49 formed in cylindrical section 31. On one surfaces of the three levers 58 opposite to the cylindrical section 31, arrow signs 58a for indicating communicating directions are respectively provided.

Note that, the number of levers included in the handle section 32 is not limited to three and may be only one, for example.

Operation of Medical Stopcock

Next, operation of the medical stopcock 1 having a configuration described above is described with reference to FIGS. 3 to 12.

Figure 6:
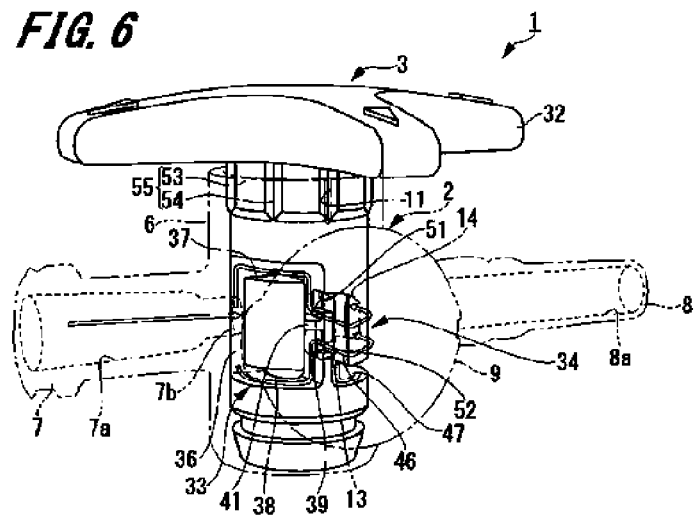
FIG. 6 is a perspective view illustrating a state of the medical stopcock according to an embodiment of the present invention where the cock is at a reference position.
Figure 7:
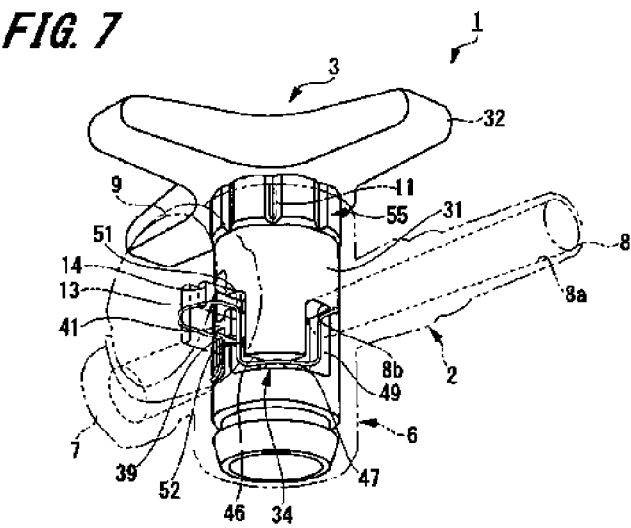
FIG. 7 is a perspective view of the medical stopcock illustrated in FIG. 6 viewed from the downstream port section side.

FIG. 6 is a perspective view illustrating a state where all of the upstream port section 7, the port section 9 for a side tube, and the downstream port section 8 communicate with each other, and FIG. 7 is a perspective view of the medical stopcock illustrated in FIG. 6 viewed from the downstream port section 8 side.

First, a state where all of the upstream port section 7, the port section 9 for a side tube, and the downstream port section 8 communicate with each other is described. Note that, the position of the cock 3 in this state is defined as a reference position.

In a state where the cock 3 is in the reference position as illustrated in FIG. 6, the upstream opening 7b formed in the body section 6 and the first liquid introduction section 36 of the cylindrical section 31 face each other. Therefore, the upstream port section 7 and the first liquid introduction section 36 communicate with each other.

In addition, as illustrated in FIG. 3, the first communication hole 13 formed in the port section 9 for a side tube and the first liquid discharge section 39 face each other, and the first communication hole 13 and the first liquid discharge section 39 communicate with each other. More specifically, the first liquid discharge section 39 and the first communication hole 13 form a flow path through which a medical solution passes. Thus, the upstream port section 7 and the first communication hole 13 of the port section 9 for a side tube communicate with each other through the first flow path groove 33 formed in the cylindrical section 31.

As illustrated in FIG. 6, a medical solution flowing from the upstream port section 7 flows through the first liquid introduction section 36 and into the first flow path groove 33 of the cylindrical section 31. The medical solution that has flown into the first flow path groove 33 passes through the first communication section 37 and the second communication section 38 and then flows to the first liquid discharge section 39.

At the first liquid discharge section 39, the first communication section 37 and the second communication section 38 are merged. At the merge part, the projection 41 is provided. Therefore, a medical solution that has flown through the first communication section 37 and the second communication section 38 hits the projection 41, whereby the flow direction is changed.

At the first liquid discharge section 39, the connection grooves 51 and 52 communicating with the second liquid introduction section 46 are formed. However, the opening area of parts of the connection grooves 51 and 52 through which a medical solution passes is smaller than the opening area of the first communication hole 13 facing the first liquid discharge section 39. Therefore, more of the medical solution flows to the first communication hole 13 side than the connection grooves 51 and 52 while being guided by the projection 41. As a result, as illustrated in FIG. 3, it is possible to make a medical solution flowing from the upstream port section 7 to flow into an internal space of the port section 9 for a side tube and a space formed between the port section 9 for a side tube and the connector 4 (hereinafter, referred to as the "Space S1").

In addition, as illustrated in FIGS. 3 and 7, the second communication hole 14 formed in the port section 9 for a side tube and the second liquid introduction section 46 face each other, and the second communication hole 14 and the second liquid introduction section 46 communicate with each other. Therefore, the second liquid introduction section 46 and the second communication hole 14 form a flow path through which a medical solution passes.

Further, the downstream opening 8b and the second liquid discharge section 49 face each other, and the downstream port section 8 and the second flow path groove 34 communicate with each other. Thus, the second communication hole 14 of the port section 9 for a side tube and the downstream port section 8 communicate with each other through the second flow path groove 34.

As illustrated in FIG. 3, a medical solution that has flown into the space S1 flows through the second communication hole 14 and into the second liquid introduction section 46, that is, the second flow path groove 34. The medical solution that has flown into the second flow path groove 34 flows through the third communication section 47 and is discharged from the second liquid discharge section 49 to the downstream port section 8.

As described above, a medical solution flowing from the upstream port section 7 to the downstream port section 8 passes through the port section 9 for a side tube, thereby generating a flow of the medical solution in the space S1. Therefore, a medical solution injected from the connector 4 to the space S1 is pushed out to the downstream port section 8 by a medical solution flowing from the upstream port section 7. As a result, a medical solution injected from the connector 4 to the port section 9 for a side tube can be prevented from staying in the space S1.

In addition, the first communication hole 13 and the second communication hole 14 are formed in the port section 9 for a side tube so as to separately form a flow path through which a medical solution flows into the space S1 and a flow path through which the medical solution is discharged from the space S1. A medical solution flowing from the upstream port section 7 thereby can flow smoothly into the space S1.

In addition, since the opening area of the second communication hole 14 is set smaller than the opening area of the first communication hole 13, a medical solution that have flown into the space S1 is hardly discharged from the second communication hole 14 directly. Therefore, the whole of the space S1 can be filled with a medical solution, and a dead space where a medical solution does not flow can be reduced in the space S1. As a result, a medical solution can be prevented from staying in the space S1, and further, a medical solution injected from the connector 4 and a medical solution flowing into the space S1 from the upstream port section 7 can be efficiently mixed in the space S1.

Further, since a dead space where a medical solution does not flow can be reduced in the space S1, upon priming, an air bubble remaining in the space S1 can be pushed out by a medical solution from the space S1 through the second communication hole 14. As a result, an air bubble hardly remains in the space S1 advantageously.

Next, a state of the medical stopcock 1 after about 45° rotation of the cock 3 from the reference position will be described with reference to FIGS. 8 to 10. In the Embodiment, an example where the cock 3 is rotated from the reference position by about 45° clockwise as seen from the handle section 32 side will be described.

FIG. 8 is a perspective view illustrating a state after 45° rotation of the cock 3 from the reference position, and FIG. 9 is a perspective view of the medical stopcock 1 illustrated in FIG. 8 as viewed from the downstream port side. FIG. 10 is a cross-sectional view taken along line T-T of FIG. 8.

The rotation of the cylindrical section 31 moves the engagement projection 11, which has been in engagement with the engagement recesses 55, over the swelling parts 54. Further rotation of the cylindrical section 31 causes the engagement projection 11 which has moved over the swelling parts 54 to engage with the engagement recesses 55. Upon engagement of the engagement projection 11 and the engagement recesses 55, a click feeling is transmitted to a user in rotary operation of the cylindrical section 31.

Since the eight swelling parts 54 are formed on the cylindrical section 31 in the Embodiment, the eight engagement recesses 55 are formed at about 45° interval along the circumferential direction of the cylindrical section 31. Therefore, every about 45° rotation of the cylindrical section 31 generates the click feeling.

Figure 10:
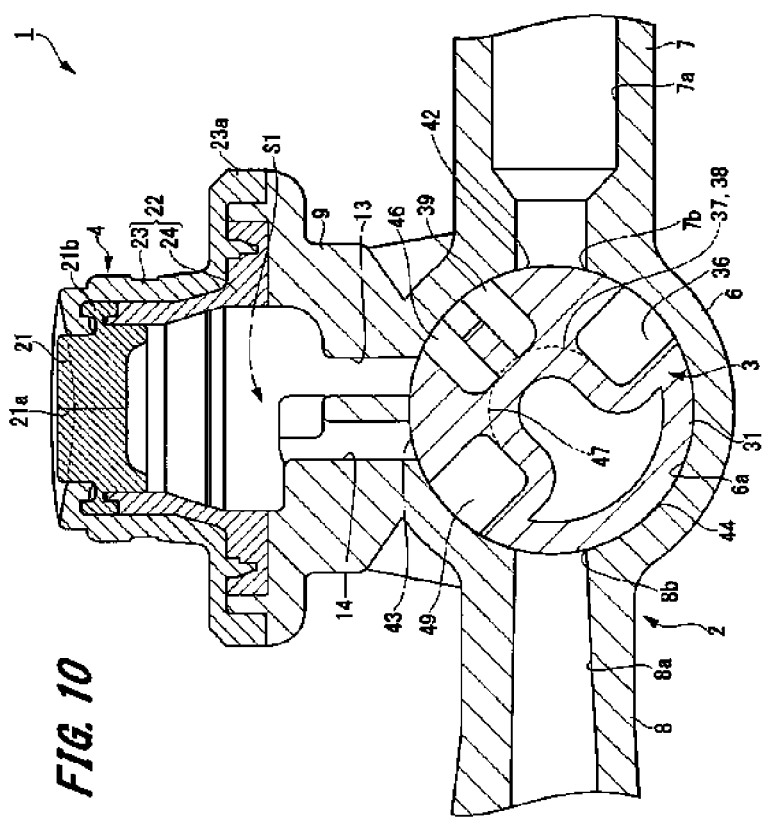
FIG. 10 is a cross-sectional view taken along line T-T illustrated in FIG. 8.

As illustrated in FIGS. 8 and 10, the upstream opening 7b faces the first closing surface 42. Therefore, the upstream port section 7 is closed at the upstream opening 7b by the first closing surface 42, whereby a medical solution is not allowed to flow therein/therefrom. In addition, the first communication hole 13 and the second communication hole 14 are closed by the second closing surface 43. Therefore, injection of a medical solution from the port section 9 for a side tube is not available.

Further, as illustrated in FIGS. 9 and 10, the downstream opening 8b is closed by the third closing surface 44. Therefore, a medical solution is not allowed to flow through the downstream port section 8. Thus, rotation of the cock 3 by a predetermined amount (about 45° from the reference position in the Embodiment) can make a closed state, in which all flow paths of the port sections 7, 8, and 9 are closed.

Counter-clockwise rotation of the cock 3 by about 45° from the reference position as seen from the handle section 32 side makes the upstream opening 7b closed by the third closing surface 44 and makes the first and second communication holes 13 and 14 closed by the first closing surface 42. In addition, the downstream opening 8b is closed by the second closing surface 43.

Next, a state of the medical stopcock 1 after counter-clockwise rotation of the cock 3 by 90° from the reference position as seen from the handle section 32 side is described with reference to FIG. 11.

Figure 11:
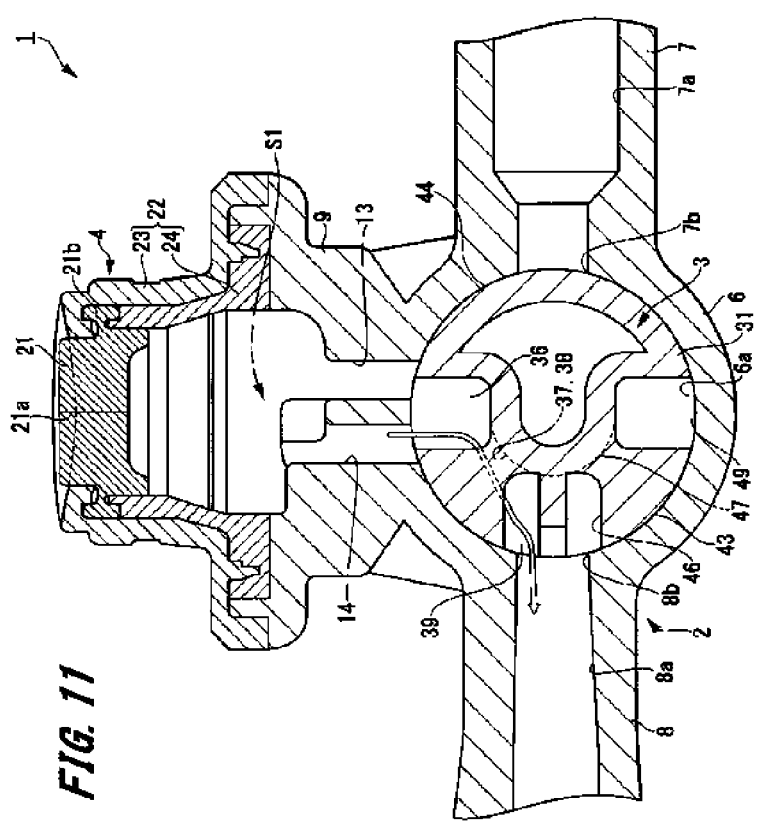
FIG. 11 is an explanatory drawing illustrating a cross section of a state after switching flow paths in the medical stopcock according to an embodiment of the present invention.

FIG. 11 is a cross-sectional view illustrating a state after counter-clockwise rotation of the cock 3 by 90° from the reference position as seen from the handle section 32 side.

As illustrated in FIG. 11, the first and second communication holes 13 and 14 formed in the port section 9 for a side tube face the first liquid introduction section 36. In addition, the downstream opening 8b faces the first liquid discharge section 39 and the second liquid introduction section 46. Therefore, the port section 9 for a side tube and the downstream port section 8 communicate with each other through the first flow path groove 33.

On the other hand, the upstream opening 7b faces the third closing surface 44 of the cylindrical section 31. More specifically, the upstream opening 7b is closed by the third closing surface 44, disabling a medical solution from flowing in/from the upstream port section 7.

Clockwise rotation of the cock 3 by about 90° from the reference position as seen from the handle section 32 makes the upstream opening 7b face the first liquid discharge section 39 and the second liquid introduction section 46. The first and second communication holes 13 and 14 of the port section 9 for a side tube face the second liquid discharge section 49. The downstream opening 8b is closed by the third closing surface 44. More specifically, the upstream port section 7 and the port section 9 for a side tube communicate with each other through the second flow path groove 34, and a medical solution does not flow in/from the downstream port section 8.

Next, a state of the medical stopcock 1 after rotation of the cock 3 by about 180° from the reference position is described with reference to FIG. 12.

Figure 12:
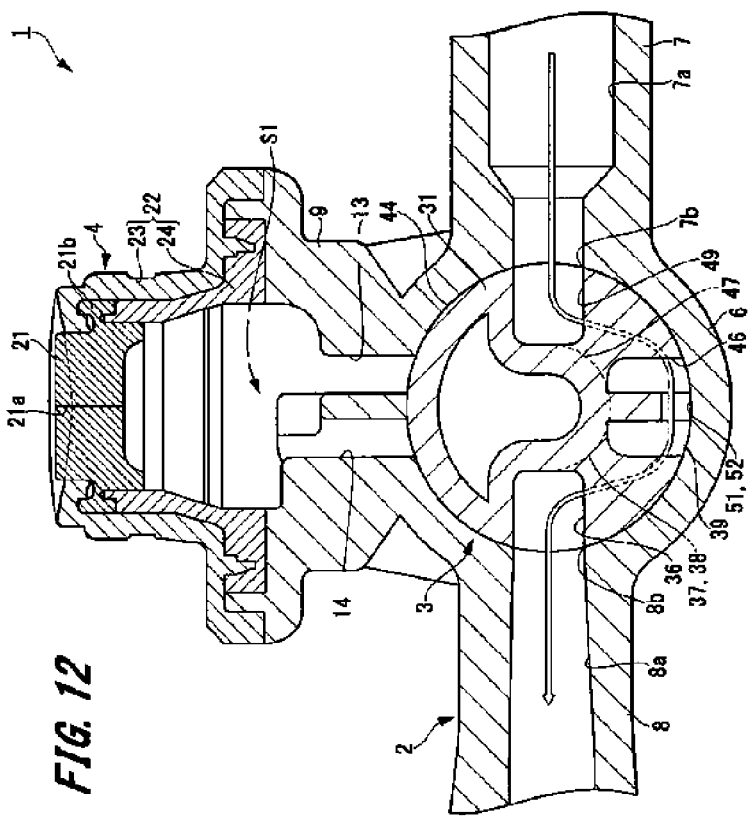
FIG. 12 is an explanatory drawing illustrating a cross section of a state after another switching of flow paths in the medical stopcock according to an embodiment of the present invention.

FIG. 12 is a cross-sectional view illustrating a state after rotation of the cock 3 by about 180° from the reference position.

As illustrated in FIG. 12, the upstream opening 7b faces the second liquid discharge section 49, and the downstream opening 8b faces the first liquid introduction section 36. The first liquid discharge section 39 and the second liquid introduction section 46 of the cylindrical section 31 face the inner peripheral surface of the through-hole 6a in the body section 6. Note that, the first liquid discharge section 39 and the second liquid introduction section 46 communicate with each other through the connection grooves 51 and 52. Thus, the upstream port section 7 and the downstream port section 8 can communicate with each other through the first flow path groove 33 and the second flow path groove 34.

The first communication hole 13 and the second communication hole 14 of the port section 9 for a side tube are closed by the third closing surface 44 of the cylindrical section 31. Therefore, injection of a medical solution from the port section 9 for a side tube is not available.

Note that, when the upstream port section 7 and the downstream port section 8 only are not made to communicate with each other by rotation of the cock 3 by 180° from the reference position, the connection grooves 51 and 52 are not necessarily provided.

The present invention is not limited to the embodiment described above and illustrated in the drawings, and various modifications can be made without departing from the scope of the invention described in the claims. For example, a partition wall may be provided at a part of the first communication hole 13, the part facing the projection 41 of the cylindrical section 31 in a state where the cock 3 is at the reference position. A medical solution thereby can be guided to the side of the port section 9 for a side tube not only by the projection 41 but also by the partition wall.

In the embodiment described above, an example, the engagement projection 11 and the engagement receiving part 53 for generating click feeling are provided respectively at one end of the body section 6 and the cylindrical section 31 in the axial direction. However, the engagement projection 11 and the engagement receiving part 53 may be provided on the other end of the body section 6 and the cylindrical section 31 in the axial direction. In addition, the engagement projection 11 may be provided on the side wall 3a of the cylindrical section 31, and the engagement receiving part 53 may be formed in the inner peripheral surface of the through-hole 6a in the body section 6.

What is claimed is:

1. A medical stopcock device comprising:
    a housing configured to allow a flow of liquid therethrough; and
    a cock configured to fit in the housing and switch flow paths of the liquid flowing through the housing,
    wherein the housing comprises:
        a cylindrical body section formed with a through-hole;
        an upstream port section provided on an outer periphery of the body section, the upstream port section comprising a female connector;
        a downstream port section provided on the outer periphery of the body section and disposed on a side of the body section that is opposite to the upstream port section; and
        a side tube port section provided between the upstream port section and the downstream port section on the outer periphery of the body section and including a first communication hole on an upstream port section side of the side tube port section, and a second communication hole on a downstream port section side of the side tube port section,
    wherein (i) a height of an inward facing wall of the side tube port section that is adjacent to the downstream port section and defines the second communication hole is greater than (ii) a height of an inward facing wall of the side tube port section that is adjacent to the upstream port section and defines the first communication hole, such that (i) an area of an opening into the second communication hole at a smallest portion of the second communication hole is smaller than (ii) an area of an opening into the first communication hole at a smallest portion of the first communication hole,
    wherein the cock comprises:
        a cylindrical section configured to be inserted in the through-hole of the body section in a slidable manner, and including a first flow path groove and a second flow path groove; and
        a handle section configured to rotate the cylindrical section, and
    wherein, when the cock is at a reference position, the upstream port section, the side tube port section, and the downstream port section communicate with each other in a manner such that the first flow path groove communicates with the upstream port section and the first communication hole in the side tube port section, and the second flow path groove communicates with the second communication hole in the side tube port section and the downstream port section.

2. The medical stopcock device according to claim 1, wherein the first flow path groove comprises:
    a liquid introduction section, configured to allow liquid to flow therein;
    a plurality of communication sections branching from the liquid introduction section; and
    a liquid discharge section, at which the branched communication sections merge, and which faces the first communication hole when the cock is at the reference position.

3. The medical stopcock device according to claim 2, wherein the liquid discharge section is provided with a projection at a portion where the communication sections merge.

4. The medical stopcock device according to claim 3, wherein, at a part of the first communication hole, a partition wall is provided, said part facing the projection when the cock is at the reference position.

5. The medical stopcock device according to claim 2, wherein the liquid discharge section and the second flow path groove communicate with each other through a connection groove.

6. The medical stopcock device according to claim 5, wherein the connection groove has an opening area smaller than that of the first communication hole and that of the second communication hole.

7. The medical stopcock device according to claim 1, wherein the cylindrical section has a closing surface configured to close the upstream port section, the side tube port section, and the downstream port section when the cock is rotated by a predetermined amount.

8. The medical stopcock device according to claim 1, wherein the second flow path groove includes a plurality of communication sections.

9. The medical stopcock device according to claim 1, further comprising a connector attached to the side tube port section.

10. The medical stopcock device according to claim 9, wherein the connector comprises a valve.

11. The medical stopcock device according to claim 7, wherein, when the cock is in a position rotated about 45 degrees from the reference position, the upstream port section, the downstream port section, and the side tube port section are closed.

12. The medical stopcock device according to claim 7, wherein, when the cock is in a position rotated about 90 degrees from the reference position, the downstream port section and the side tube port section communicate with each other and the upstream port section is closed.

13. The medical stopcock device according to claim 7, wherein when the cock is in a position rotated about 180 degrees from the reference position, the upstream port section and the downstream port section communicate with each other and the side tube port section is closed.

* * * * *